(12) United States Patent
Gruhl

(10) Patent No.: US 6,658,278 B2
(45) Date of Patent: Dec. 2, 2003

(54) STEERABLE INFRARED IMAGING CATHETER HAVING STEERING FINS

(75) Inventor: Fred Gruhl, Ann Arbor, MI (US)

(73) Assignee: Terumo Cardiovascular Systems Corporation, Ann Arbor, MI (US)

( * ) Notice: Subject to any disclaimer, the term of this patent is extended or adjusted under 35 U.S.C. 154(b) by 0 days.

(21) Appl. No.: 09/977,948

(22) Filed: Oct. 17, 2001

(65) Prior Publication Data

US 2003/0073909 A1 Apr. 17, 2003

(51) Int. Cl.⁷ .................................................. A61B 5/00
(52) U.S. Cl. .................... 600/407; 600/473; 600/478
(58) Field of Search .............................. 600/407, 473, 600/475–478, 342, 109, 129, 160, 170; 604/95.03

(56) References Cited

U.S. PATENT DOCUMENTS

| | | |
|---|---|---|
| 5,445,157 A | 8/1995 | Adachi et al. |
| 6,178,346 B1 | 1/2001 | Amundson et al. |
| 2002/0183620 A1 * | 12/2002 | Tearney et al. ............. 600/473 |

* cited by examiner

*Primary Examiner*—Ruth S. Smith
(74) *Attorney, Agent, or Firm*—Burns, Doane, Swecker & Mathis, LLP

(57) ABSTRACT

A lumen wall of a blood vessel, such as a coronary artery, is imaged by inserting a catheter into the vessel and emitting near-IR radiation toward the lumen wall through a side window formed in the catheter. Blood flowing through the vessel is caused to react with a fin arrangement formed on a body of the catheter to displace the window toward a region of the lumen wall opposing the window in order to minimize the amount of blood that is interposed between the window and the lumen wall. Thus, the amount of radiation that is scattered or absorbed by the blood is minimized.

5 Claims, 3 Drawing Sheets

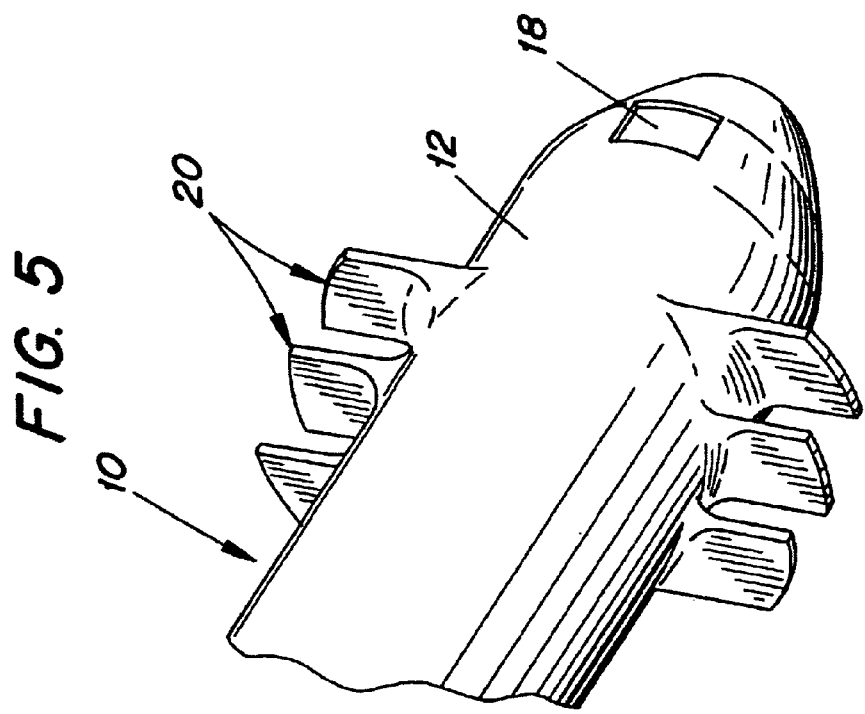
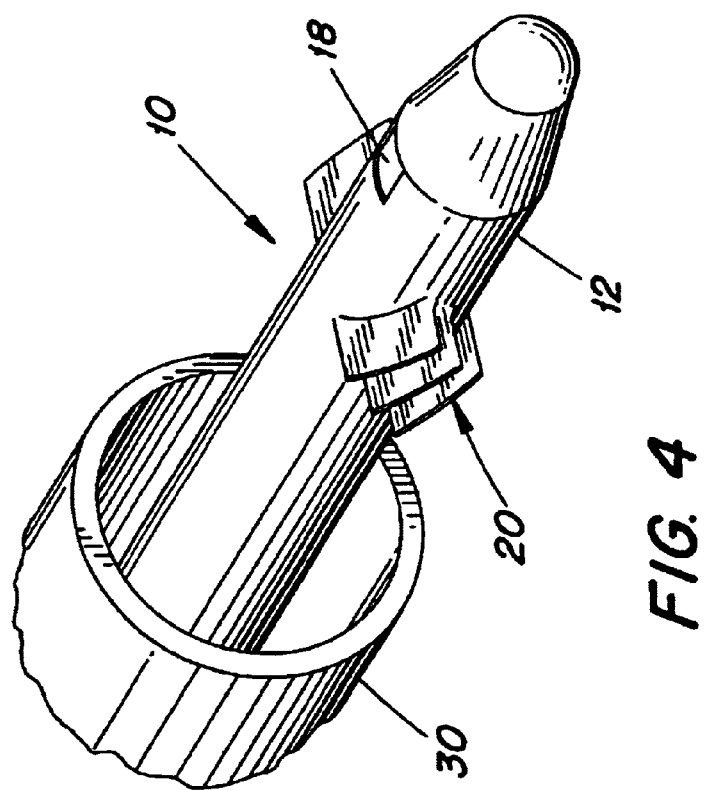

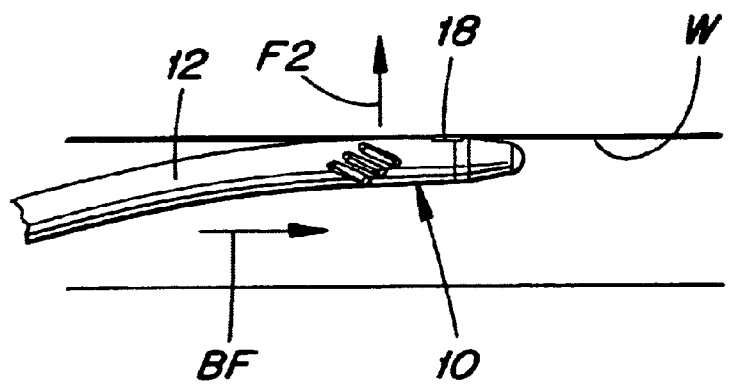
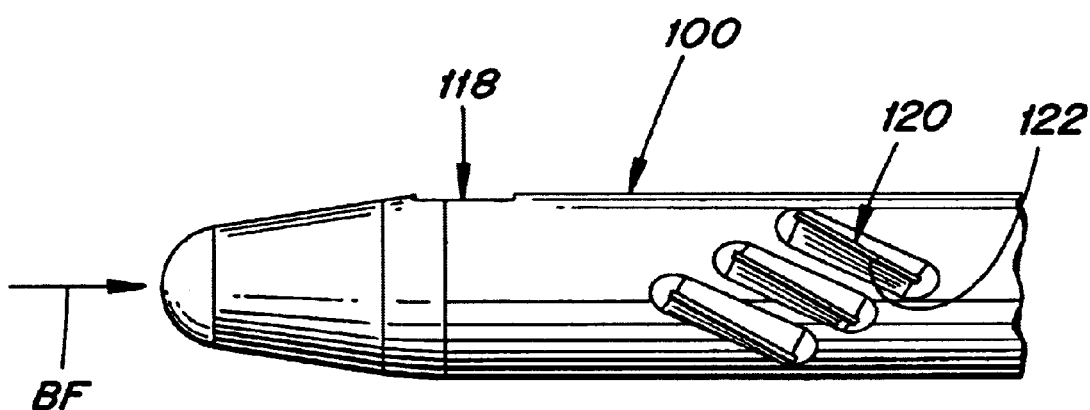

STEERABLE INFRARED IMAGING CATHETER HAVING STEERING FINS

BACKGROUND OF THE INVENTION

The present invention relates to the use of catheters in performing infrared imaging to inspect and characterize the lumen of a blood vessel, especially a coronary artery.

Visual imaging of internal body structures has heretofore been performed in certain medical procedures. For example, visual imaging by means of endoscopes introduced into the body has been useful in guiding the movements of certain medical devices inserted into the body for body treatment, and to view the results.

It is necessary that the body region in which the visual imaging, or endoscopy, is to be performed, contain a fluid that is transparent to the light wavelengths being utilized. Thus, visual imaging within body cavities such as the stomach can be performed after evacuating the stomach.

A form of endoscopy, called angioscopy, has been performed in coronary arteries. However, substances in the blood can obscure the image. For example, light can be scattered by red blood cells and absorbed by hemoglobin in the blood. Accordingly, it has been required that blood first be removed from the arterial region being inspected, and replaced with a clear saline solution which is transparent to the light wavelength. Difficulties such as this in obtaining a clear image have limited the usefulness of visual imaging of blood vessels.

The imaging of internal body cavities has also been performed by sensing infrared radiation emitted from body structures (see U.S. Pat. Nos. 5,445,157 and 6,178,346). In U.S. Pat. No. 6,178,346 for example, it has been proposed to inspect the lumen of a coronary artery by introducing into the artery a catheter which emits infrared light toward the wall of the lumen. Light that is reflected from the lumen wall is directed to an infrared camera so that a real-time image of the lumen wall can be formed. Such a procedure enables physicians to identify potentially dangerous plaque build-up and lesions on the lumen wall, and specifically identify characteristics of vulnerable plaque in the lumen wall).

It would be desirable to provide improved methods and apparatus for imaging a lumen of a blood vessel, such as a coronary artery using light of any suitable wavelength, intensity and duration, chosen independently of the light-absorption and light-scattering characteristics of blood.

It would also be desirable to provide such methods and apparatus which can utilize relatively low intensity light in the near infrared region, especially 0.8 to 1.4 microns.

SUMMARY OF THE INVENTION

The present invention relates to a catheter for imaging a lumen of a blood vessel, such as a coronary artery. A catheter includes a catheter body which has a lateral window adjacent a tip of the body. A fiber optic cable is disposed in the body for transmitting light. An optical head is disposed adjacent the window for transmitting the light through the window and toward a wall of the lumen and for receiving reflected light from the lumen wall and transmitting the received reflective light to the cable. A deflector arrangement is disposed on a external surface of the catheter body adjacent the window for interacting with a flow of blood through the vessel to displace the window laterally toward a region of the lumen wall opposing the window, to minimize the amount of blood disposed between the window and the lumen wall.

The invention also pertains to a method of imaging a wall of a lumen of a blood vessel. The method comprises the steps of:

A) inserting a catheter body into the vessel;
B) emitting radiation through a side window formed in an outer periphery of the body;
C) receiving radiation reflected off the lumen wall and transmitting the radiation to imaging equipment; and
D) causing a deflector arrangement on the body to react with blood flowing through the vessel to displace the window toward a region of the lumen wall opposing the window to thereby minimizing the amount of blood disposed between the window and the lumen wall.

BRIEF DESCRIPTION OF THE DRAWING FIGURES

The objects and advantages of the invention will become apparent from the following detailed description of preferred embodiments thereof in connection with the accompanying drawings in which like numerals designate like elements and in which:

FIG. 4 is a front perspective view of the catheter emerging from a sheath;

FIG. 5 is a rear perspective view of the catheter of FIG. 1;

FIG. 6 is a schematic view depicting the manner of operation of the catheter in a blood vessel; and FIG. 7 is a view similar to FIG. 2 of a modified catheter.

DETAILED DESCRIPTION OF A PREFERRED EMBODIMENT OF THE INVENTION

Figure 3:
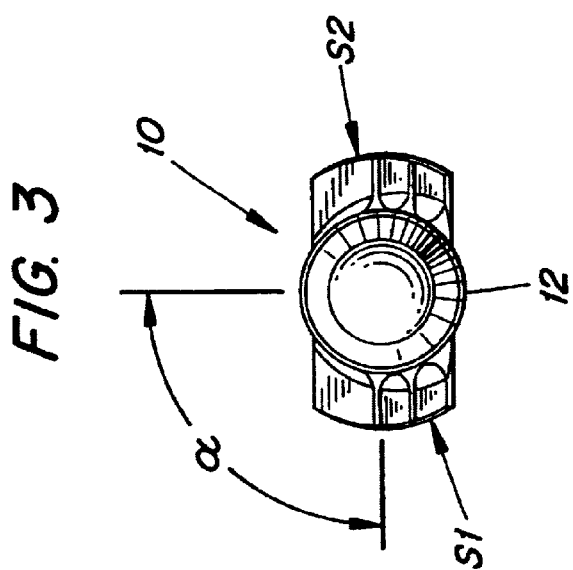
FIG. 3 is a front end view of the catheter of FIG. 1.
Figure 1:
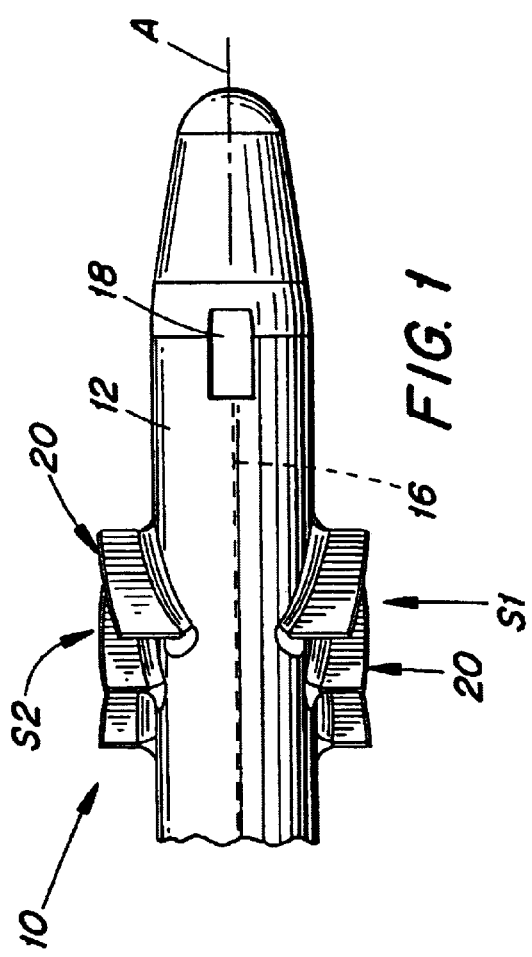
FIG. 1 is a side elevational view of a front end of a catheter according to the present invention.
Figure 2:
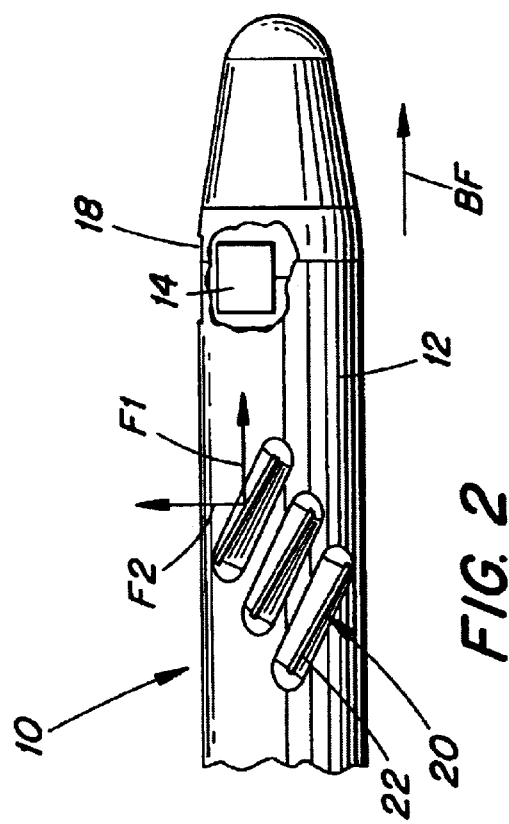
FIG. 2 is a view similar to FIG. 1, but taken at a location spaced 90 degrees from that of FIG. 1, and with a portion of the catheter wall broken away.

Depicted in FIGS. 1–5 is an infrared endoscope catheter 10 according to the present invention. The catheter 10 is similar to a conventional visible-region endoscope in that it includes a tubular body 12 containing an optical head 14, and a fiber optic cable 16. The cable 16 transmits IR (infrared) radiation from an IR source to the optical head, and then transmitting away from the optical head the IR radiation that has been reflected from the wall W of a human body part, in this case a lumen of a blood vessel, such as a coronary artery lumen (see FIG. 6). The optic head comprises a conventional lens arrangement for emitting the IR radiation (preferably near-IR radiation) laterally from the catheter through a side window 18 disposed in a front portion of the body 12. After being reflected from the lumen wall, the near-IR radiation is received by the lens arrangement and transmitted out of the catheter back through the fiber optic cable. That radiation is then transmitted to a conventional infrared camera (not shown) and converted to an electric signal that can be used to form an image in conventional image processing equipment (not shown).

As explained earlier, substances in the blood, especially red cells, hemoglobin can render the blood opaque to the near-IR radiation. Accordingly, the catheter 10 includes a deflector structure, preferably an arrangement of fins 20, which reacts with the force of flowing blood to deflect the side window laterally toward the region of the lumen wall facing the window, thereby minimizing the amount of blood interposed between the window and the lumen wall.

The fin arrangement comprises diametrically opposite fins, preferably two diametrically opposite fin sets S1, S2, each set containing three fins 20. Each fin 20 is oriented obliquely relative to a longitudinal axis A of the catheter, and thus obliquely relative to the direction of blood flow BF (see FIG. 6). In particular, each fin is inclined in a direction such that the front end of each fin, i.e., the end closest to the tip (front end) of the catheter, is directed toward the side of the catheter opposite the side in which the window 18 is formed. As a result, the blood flow will apply to each fin a force having an axially forward component F1, and a laterally outward component F2 directed toward the region of the lumen wall facing the window 18. The component F2 displaces the front portion of the catheter laterally toward that region of the lumen wall, as shown in FIG. 6.

The window 18 is situated on a portion of the outer circumference of the catheter body that is spaced circumferentially from each set of fins by an angle ∝ of about ninety degrees as the catheter is viewed from the end (see FIG. 3). Thus, the window can closely approach the lumen wall when the front portion of the catheter is deflected toward the lumen wall (see FIG. 6). Consequently, the amount of blood situated between the window 18 and the lumen wall is minimized to facilitate the ability of the optical head 14 to transmit IR radiation toward the lumen wall and receive the radiation that is reflected from that wall, i.e., the tendency for the radiation to be scattered or absorbed by substances in the blood is minimized.

In practice, the catheter 10 is fed into the blood vessel through a sheath 30 (FIG. 4) as is conventional. Due to force component F2 generated as the blood flow acts against the fins 20, the front portion window 18 will be displaced laterally to the lumen wall. As imaging is performed by the emission of near-IR radiation, the catheter is advanced and is rotated about its axis A to enable the entire inner circumference of the lumen wall to be inspected. In order to image the entire lumen wall, the window 18 should track the lumen wall during catheter rotation. When utilizing a catheter according to the present invention, the rate of rotation of the catheter should be slow enough to provide sufficient time for the deflected front portion of the catheter to adapt to force changes applied to the fins during the catheter rotation and remain disposed at the lumen wall. The optimum speed of catheter rotation will vary, depending upon various factors such as the speed of blood flow. Generally speaking, the rate of rotation should probably be less than 2 rps (revolutions per second) and possibly even as low as 0.5 rps.

The number of fins and the orientation of the fins relative to the catheter body and to each other can vary. It has been found for example, that two fins per set are preferable to one fin per set, and three fins per set are preferable to two fins per set. By varying the angle of inclination between the fins and the axis A, as the catheter is viewed from the side (see FIG. 2), the magnitude of the force F2 can be altered.

The shape of the catheter body may vary. For example, the tip of the catheter body could be enlarged, rather than narrowed as shown.

The shape of the fins can vary. Instead of being flat, the fins could be curved, preferably to present a concave surface opposing the direction of blood flow BF.

A cowl could be wound around the circumference of the catheter body to encompass the fins in order to direct blood flow to the fins. This could also serve to protect the vessel lumen wall.

When inserted into a coronary artery, the catheter will be introduced from the sheath in the same direction as the blood flow BF. The speed of the blood flow is sufficiently great to generate a high enough force F2 for deflecting the front portion of the catheter to the lumen wall W. Sufficient blood speed also exists in the aorta and the carotid arteries to enable the catheter to be used there as well.

The catheter may be able to function in blood vessels where the blood flow rate is significantly less, e.g., in veins, by displacing the catheter through the vessel in a direction opposite the direction of blood flow, thereby increasing the blood flow rate relative to the fins for generating a higher force F2. Such a catheter 100 is depicted in FIG. 7. It will be appreciated that the orientation of the fins 120 must be altered from that of the fins 20 of the previously described embodiment. That is, the fins 120 must be oriented such that the forward end of each fin (i.e., the end closest to the tip of the catheter) is directed toward the side of the catheter body in which the window is formed.

It will be appreciated that the present invention enables light of any suitable wavelength, intensity and duration to be employed in imaging a blood vessel wall, with minimal risk of scattering and absorption.

Although the present invention has been described in connection with preferred embodiments thereof, it will be appreciated by those skilled in the art that additions, deletions, modifications, and substitutions not specifically described may be made without departing from the spirit and scope of the invention as defined in the appended claims.

What is claimed is:

1. A catheter for imaging a lumen wall of a blood vessel comprising:
   a catheter body including a lateral window disposed in a front portion of the body;
   a fiber optic cable disposed in the body for transmitting light;
   an optical head disposed adjacent the window for transmitting the light through the window and toward the lumen wall and for receiving reflected light from the lumen wall and transmitting the received reflected light to the cable; and
   a deflector arrangement projecting from an external surface of the catheter body adjacent the window for interacting with a flow of blood through the vessel to displace the window laterally toward a region of the lumen wall opposing the window, to minimize an amount of blood disposed between the window and the lumen wall;
   wherein the deflector arrangement comprises fins disposed on opposite sides of the catheter body and arranged to be displaced toward the lumen wall by the force of blood flow.

2. The catheter according to claim 1 wherein the deflector arrangement includes at least first and second fins disposed on respective opposite sides of the catheter body, the window disposed circumferentially between the first and second fins as the catheter body is viewed from an end thereof.

3. The catheter according to claim 1 wherein the fins are generally diametrically opposed on the catheter body.

4. The catheter according to claim 3 wherein there are two sets of diametrically opposed fins, each set comprising a plurality of fins.

5. The catheter according to claim 1 wherein each fin extends in a direction inclined obliquely relative to a longitudinal axis of the catheter, as the catheter is viewed from the side.

* * * * *